United States Patent [19]

Pilgram

[11] 4,108,399

[45] Aug. 22, 1978

[54] HERBICIDAL SEMICARBAZONES

[75] Inventor: Kurt H. G. Pilgram, Modesto, Calif.

[73] Assignee: Shell Oil Company, Houston, Tex.

[21] Appl. No.: 466,103

[22] Filed: May 2, 1974

Related U.S. Application Data

[63] Continuation-in-part of Ser. No. 283,686, Aug. 25, 1972, abandoned.

[51] Int. Cl.² ............................................ C07C 133/02
[52] U.S. Cl. .............................. 542/417; 260/295 E; 260/453 RW; 260/554; 71/88; 71/90; 71/94; 71/120
[58] Field of Search ...................... 260/347.3, 554, 295, 260/332.2, 453; 542/417

[56] References Cited

U.S. PATENT DOCUMENTS

| 3,712,914 | 1/1973 | Tilles | 260/554 |
| 3,776,955 | 12/1973 | Zielinski | 260/554 |

FOREIGN PATENT DOCUMENTS

| 7,010,689 | 1/1972 | Netherlands | 260/554 |

OTHER PUBLICATIONS

Pyl et al., J. fur Prakt. Chem., vol. 20, pp. 255–262 (1963).
Mautner et al., Chem. Abst., vol. 50, col. 12870–12871 (1956).
Schantl, Chem. Abst., vol. 72, item 12304 (1970).

Primary Examiner—Henry R. Jiles
Assistant Examiner—R. W. Ramsuer

[57] ABSTRACT

2-Phenylsemicarbazones of the formula

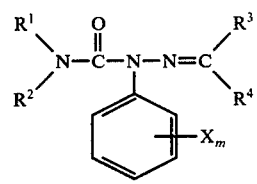

are useful as herbicides. The 2-phenylsemicarbazones are prepared by reaction of a phenylhydrazone with a strong base followed by reaction with a carbamoyl chloride or an alkyl isocyanate.

5 Claims, No Drawings

HERBICIDAL SEMICARBAZONES

CROSS-REFERENCE TO RELATED APPLICATIONS

This application is a continuation-in-part of Ser. No. 283,686, filed Aug. 25, 1972, now abandoned.

BACKGROUND OF THE INVENTION

1. Field of the Invention

This invention relates to new herbicides and to herbicidal compositions containing said herbicides. More specifically, this invention relates to a new class of 2-phenylsemicarbazones, a new method for preparation of said 2-phenylsemicarbazones, and to a new method for controlling undesirable plant growth using said 2-phenylsemicarbazones.

2. Description of the Prior Art

Netherlands application No. 69,00033 discloses certain N-carboxylic acid derivatives of 1,2-dicarbonyl-phenylhydrazones, useful as insecticides and acaricides. Netherlands application No. 7,010,689 discloses benzaldehyde, 2-(3,4-dichlorophenyl)-4,4-dimethylsemicarbazone as an intermediate for herbicides.

SUMMARY OF THE INVENTION

The novel compounds of this invention are represented by the formula

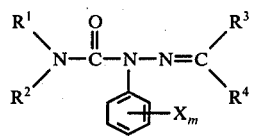 (I)

where $R^1$ and $R^2$ are each hydrogen, alkyl, or alkoxy; $R^3$ and $R^4$ are each hydrogen, alkyl, haloalkyl, aryl optionally substituted by one or more halogen or trifluoromethyl groups, a heteroaromatic group selected from thienyl, furyl or pyridyl; or together $R^3$ and $R^4$ can form an alkylene bridge; X is halogen, alkyl or alkoxy wherein the alkyl portion may be substituted by one or more halogens; and $m$ is 0 to 5.

The 2-phenylsemicarbazones of this invention can be prepared by reaction of the appropriate phenylhydrazone with an alkyl isocyanate or with a strong base followed by reaction with a carbamoyl chloride.

Herbicidal compositions of this invention comprise a compound within the scope of the invention and an inert, agriculturally acceptable carrier therefor. Undesirable plant growth is destroyed or prevented by applying the compounds of the invention, ordinarily in a herbicidal composition of one of the aforementioned types, to either the unwanted plant growth itself or to the area to be kept free of such unwanted growth.

The 2-phenylsemicarbazones are also useful as intermediates for certain herbicidal 2-phenylsemicarbazides. For a more detailed description of these 2-phenylsemicarbazides, see Ser. No. 283,687, filed Aug. 25, 1972, now abandoned the disclosure of which is hereby incorporated by reference.

DETAILED DESCRIPTION OF THE INVENTION

Typical novel compounds of this invention are those of Formula I above wherein $R^1$ and $R^2$ are each hydrogen, alkyl of 1 to 4 carbon atoms, for example, methyl, ethyl, isopropyl, tert-butyl, and the like, or alkoxy of 1 to 4 carbon atoms, for example, methoxy, ethoxy, propoxy, and the like; $R^3$ and $R^4$ are each hydrogen, alkyl of 1 to 4 carbon atoms, optionally substituted by one or more halogen or trifluoromethyl groups, for example, phenyl, styryl, benzyl, naphthyl, tolyl, 3-trifluoromethylphenyl, and the like, or heteroaromatic such as pyridyl, furyl, or thienyl; or $R^3$ and $R^4$ together form an alkylene bridge of the formula $-CHR^5-(CH_2)_n-CHR^5$ in which $R^5$ is hydrogen or alkyl of 1 to 4 carbon atoms and $n$ is 1, 2 or 3; X is halogen of atomic number 9 to 35 inclusive, alkyl or alkoxy wherein the alkyl portion contains 1 to 4 carbon atoms and may be substituted by one or more halogen atoms, for example, trifluoromethoxy, and the like; and $m$ is 0 to 5.

Typical compounds contemplated for use within the scope of this invention are:

cyclohexanone, 2-(4-bromo-3-tolyl)-4-methoxy-4-methylsemicarbazone acetaldehyde, trifluoro, 2-(2,4-dichloro-3-butoxyphenyl)4-methylsemicarbazone acetone, 2-(4-bromo-3-fluorophenyl)-4-ethoxy-4-methylsemicarbazone 2-propanone, hexachloro-, 2-(3-chloro-4-fluorophenyl)-4,4-dimethylsemicarbazone 2-pyridinecarboxaldehyde, 3,6-dichloro-, 2-(3-chloro-4-isopropoxyphenyl)-4,4-dimethylsemicarbazone benzaldehyde, 2,6-dichloro-, 2-(3-chloro-4-iodophenyl)-4,4-dimethylsemicarbazone Preferred because of their especially effective herbicidal properties and their ability to control weeds at relatively low dosages are those semicarbazones of Formula I wherein $R^1$ and $R^2$ are each alkyl of 1 to 4 carbon atoms, $R^3$ is hydrogen or alkyl of 1 to 4 carbon atoms, $R^4$ is phenyl, 3-trifluoromethylphenyl, furyl, trichloromethyl, or $R^3$ and $R^4$ together form an alkylene bridge, X is trifluoromethyl, trifluoromethoxy, or halogen, and $m$ is 0 to 2. Typical compounds of this subclass include: chloral, 2-(3,4-dichlorophenyl)-4,4-dimethylsemicarbazone; benzaldehyde, 4,4-dimethyl-2-phenylsemicarbazone; and 3-trifluoromethylbenzaldehyde, 4,4-dimethyl-2-(3-trifluoromethylphenyl)semicarbazone.

The herbicidal compounds of this invention can be prepared by three methods. Each uses a phenylhydrazone, prepared from the appropriate phenylhydrazine and a ketone, as the starting material.

According to one method, the phenylhydrazone is treated with phosgene in a non-hydroxylic solvent such as benzene, toluene, xylene, tetrahydrofuran, or ethyl acetate and in the presence of a tertiary base acceptor such as triethylamine, pyridine, picoline, or collidine, for the by-product hydrogen chloride, to yield an N-(benzylideneamino)carbanilic acid chloride of the formula

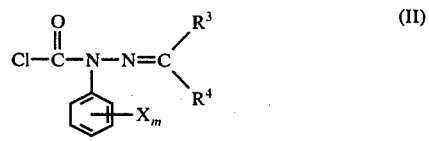 (II)

To insure that the reaction proceeds to completion, it is preferred to have at least an equimolar ratio of phosgene to phenylhydrazone (mole ratio of phosgene to hydrazone 1:1). The mole ratio of phosgene to hydrazone may be as high as 2:1 or more but no particular advantage results therefrom. Particularly preferred is the mole ratio range between about 1.1:1 to 1.5:1.

Since one mole of hydrogen chloride forms for each mole of phosgene reacted, it is preferable to use at least an equimolar ratio of tertiary base acceptor to phosgene.

The carbanilic acid chloride is then treated with at least an equimolar ratio of ammonia or an amine. Since one additional mole of hydrogen chloride forms for each mole of carbanilic acid chloride reacted, it is again desirable to have an acceptor for this by-product hydrogen halide present. The acceptor may be the ammonia or amine used as a reactant in which case a ratio at least two moles and preferably 2.1 to 2.5 moles of the ammonia or amine is preferred for each mole of acid chloride or if only an equimolar quantity of chloride to ammonia or amine is used, an additional mole of a tertiary amine, such as triethylamine, pyridine, picoline or collidine should be present for each mole of acid chloride.

The reaction is suitably carried out at a temperature of from $-10°$ to $+50°$.

It is preferred to use atmospheric pressure for the reaction; however, under certain circumstances, it may be desirable to use super or sub-atmospheric pressure.

The time required for the reaction to go to completion may be from 0.1 to about 5 hours. However, the usual time required for the reaction to go to completion will be about 0.5 to 2 hours.

Alternatively, in preparing 2-phenylsemicarbazones of Formula I wherein $R^1$ is alkyl and $R^2$ is hydrogen, the phenylhydrazone is treated with an alkyl isocyanate in at least equimolar (1:1) ratio of isocyanate to hydrazone and preferably in a ratio of from 1.1:1 to 1.5:1 to insure that the reaction proceeds to completion.

The reaction is suitably carried out at a temperature of about 50° C to 150° C and at atmospheric pressure although higher or lower temperatures and sub- or super-atmospheric pressures can be used if the other reaction conditions are adjusted accordingly.

The reaction proceeds to completion in about one to five days.

In the method of preparation preferred because of its ease of operation and speed, a phenylhydrazone is treated with a strong base such as sodium hydride, sodium methoxide, or butyl lithium in solution in a solvent, such as dimethylformamide, sulfolane, acetonitrile, or dimethylsulfoxide, forming the intermediate

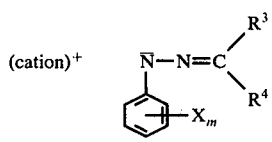

and then further treated with a carbamoyl chloride of the formula

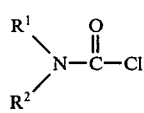

to yield the desired semicarbazone.

The ratios of base to hydrazone and carbamoyl chloride to intermediate should be at least equimolar (1:1) and preferably 1.1:1 to 1.5:1 to insure that each step of the reaction proceeds to completion.

Both reactions are suitably carried out at a temperature of 0° to 100° C and at atmospheric pressure. Sub- or super-atmospheric pressures may be used although no particular advantage results therefrom.

The reaction usually proceeds to completion in about 1 to 10 hours.

Compounds of this invention, for example, chloral, 2-(3,4-dichlorophenyl)-4,4-dimethylsemicarbazone; benzaldehyde, 4,4-dimethyl-2-phenylsemicarbazone; and 3-trifluoromethylbenzaldehyde, 4,4-dimethyl-2-(3-trifluoromethylphenyl)semi-carbazone, have been found to be active herbicides of a general type. That is, certain members of the class have been found to be herbicidally effective against a wide range of plant species. Others of the class are effective only against a limited number of plant species and are considered to be selective herbicides. Some of the compounds exhibit a high degree of herbicidal activity in the control of a variety of economically important species of grasses and broad-leaved weeds. Some of the compounds are particularly useful as selective herbicides for use in certain important crops.

The invention includes herbicidal compositions comprising a carrier or a surface-active agent, or both a carrier and a surface-active agent, and, as active ingredient, at least one 2-phenylsemicarbazone of Formula I. Likewise, the invention also includes a method of combatting weeds which comprises applying to the locus a herbicidally effective amount of a 2-phenylsemicarbazone or composition of the invention.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates for example natural silicas such as diatomaceous earths; magnesium silicates, for example, talcs; magnesium aluminum silicates, for example, attapulgites and vermiculites; aluminum silicates, for example, kaolinites, montmorillinites and micas; calcium carbonates; calcium sulfate, synthetic hydrated silicon oxides and synthetic calcium or aluminum silicates; elements sush as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax and chlorinated mineral waxes; and solid fertilizers, for example, superphosphates.

Examples of suitable fluid carriers are water, alcohols, such as for example, isopropanol, glycols; ketones, such as for example, acetone, methyl ethyl ketone, methyl isobutyl ketone and cyclohexanone; ethers, aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated caster oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, and where necessary, 0–15% by weight of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½ – 10% by weight of toxicant. Granules are usually prepared to have a size between 10 and 100 BS mesh (1.676 – 0.152 mm), and may be manufactured by agglomeration or impregnation techniques. Generally granules will contain ½ – 25% by weight toxicant and 0 – 10% by weight of additives such as stabilizers, slow release modifiers and binding agents. Emulsifiable concentrates usually contain, in addition to the solvent, and when necessary, co-solvent, 10–15% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% w toxicant, 0.5 – 15% w of dispersing agents, 0.1 – 10% w of suspending agents such as protective colloids and thixotropic agents, 0 – 10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal, properties.

The method of applying the compositions of this invention comprises applying a 2-phenylsemicarbazone, ordinarily in a herbicidal composition of one of the aforementioned types, to a locus or area to be protected from undesirable plant growth. The active compound of course is applied in amounts sufficient to exert the desired herbicidal action.

The amount of the 2-phenylsemicarbazone to be used in controlling undesirable vegetation wll naturally depend on the condition of the vegetation, the degree of herbicidal activity desired, the formulation used, the mode of application, the climate, the season of the year, and other variables. Recommendations as to precise amounts are, therefore, not possible. In general, however, application to the locus to be protected of from 0.5 to 10 pounds per acre of the herbicidal compounds used in this invention will be satisfactory.

The preparation and some of the properties of the novel 2-phenylsemicarbazones of the invention are illustrated by the following examples. It should be understood, however, that the examples given are for the purpose of illustration only, and are not to be regarded as limiting the invention in any way. In the examples below, the structure of all the products prepared was confirmed by elemental, nuclear magnetic resonance, and infrared analyses.

EXAMPLE 1

A glass cylinder was charged with 15.7 grams of benzaldehyde phenylhydrazone, 75 milliliters of tetrahydrofuran, 3 drops of triethylamine, and 15 milliliters of methyl isocyanate. The sealed cylinder was placed into a steam bath and heated at 100° C for 5 days. The reaction mixture was then cooled and concentrated to dryness. The residual solid was purified by silica chromatography to give 13.2 grams of colorless crystalline solid melting at 138°–140° C, representing a 66% yield of benzaldehyde, 4-methyl-2-phenylsemicarbazone.

EXAMPLE 2

To a solution of 11.6 grams of 4,4-dimethyl-2-(3-chloro-4-fluorophenyl)semicarbazide in 200 milliliters of benzene was added 14.7 grams of chloral and a catalytic amount of p-toluene sulfonic acid. This mixture was stirred and heated at reflux for 18 hours. The solvent was removed in vacuo leaving 18 grams (99.5% yield) of trichloroacetaldehyde, 4,4-dimethyl-2-(3-chloro-4-fluorophenyl)semicarbazone as an amber syrup.

EXAMPLE 3

To a solution of 30 grams of N-(benzlideneamino)-2',4'-dichlorocarbanilic acid chloride in benzene was added anhydrous ammonia until the mixture was distinctly basic. The temperature was controlled at 30° ± 5° using an ice bath. The mixture was stirred for 30 minutes. The precipitate was controlled on a filter. The filtrate was washed with cold dilute hydrochloric acid. The organic fraction was dried ($Mg_2SO_4$), filtered and concentrated to a solid. The solid was recrystallized from aqueous methanol to yield 17 grams (60% yield) of an off-white solid, benzaldehyde, 2-(3,4-dichlorophenyl)semicarbazone, having a melting point of 196°–198°.

EXAMPLE 4

Using the experimental procedure of Example 3, benzaldehyde, 4-methyl-2-(3,4-dichlorophenyl)semicarbazone, melting at 174°–177° C, was prepared in 60% yield.

EXAMPLE 5

To a chilled solution of 15 grams of O,N-dimethylhydroxylamine hydrochloride in 25 milliliters water was added 6 grams sodium hydroxide in 25 milliliters water. 50 milliliters tetrahydrofuran was added. The resultant mixture was stirred and chilled to 5° during rapid addition of 34.4 grams N-benzylideneamino)-4'-fluoro-3'-(trifluoromethyl)carbaniloyl chloride in 100 milliliters tetrahydrofuran. After stirring for 2 hours the products were phase separated. The organic layer was washed with water and extracted into ether. The ethered fraction was dried ($Mg_2SO_4$), filtered and concentrated to 33 grams of amber oil. The oil was purified by silica chromatography to give 21 grams of benzaldehyde, 2-(4-fluoro-3-(trifluoromethyl)phenyl)-4-methoxy-4-methyl semicarbazone as a light amber oil with melting point 78°–81°.

EXAMPLE 6

Using the experimental procedure of Example 5, benzaldehyde, 2-(4-chloro-3-(trifluoromethyl)phenyl)-4-methoxy-4-methyl semicarbazone was prepared (34.4% yield) as a light amber syrup.

EXAMPLE 7

To a stirred solution of 76.0 grams of benzaldehyde phenylhydrazone in 1 liter of dimethylformamide was added at ambient temperature portionwise 35 grams of 57% sodium hydride in mineral oil. After the evolution of hydrogen had ceased, the reaction mixture was briefly heated to 90° C and then cooled to 20° C while 58 grams of dimethylcarbamoyl chloride was added gradually through a dropping funnel. After 2 hours, the reaction mixture was poured over ice water and extracted with ether. The combined ether extracts were washed with water, dried, filtered, and concentrated to dryness to give 73.1 grams (72% yield) of benzaldehyde, 4,4-dimethyl-2-phenylsemicarbazone as an amber viscous liquid.

EXAMPLES 8–13

Using the experimental procedure of Example 7, the compounds of Table 1 were prepared:

TABLE I

2-Phenylsemicarbazones $$R^1\diagdown \underset{R^2}{N}-\overset{O}{\overset{\|}{C}}-N-N=C\diagup \underset{R^4}{\overset{R^3}{}}$$ (phenyl-$X_m$)

| Ex. No. | $R^1$ | $R^2$ | $R^3$ | $R^4$ | X | Yield % | Melting Point, °C |
|---|---|---|---|---|---|---|---|
| 8 | $CH_3$ | $CH_3$ | H | $C_6H_5$ | 3-$CF_3$ | 62 | (a) |
| 9 | H | $CH_3$ | H | $C_6H_5$ | 3-$CF_3$ | 84 | 118–120 |
| 10 | $CH_3$ | $CH_3$ | $CH_3$ | (3-$CF_3$)$C_6H_4$ | 3-$CF_3$ | 36 | (a) |
| 11 | $CH_3$ | $CH_3$ | H | $C_6H_5$ | 3-$OCF_3$ | 94 | (a) |
| 12 | $CH_3$ | $CH_3$ | H | $C_6H_5$ | 3,4-$Cl_2$ | 85 | 94–95 |
| 13 | $CH_3$ | $OCH_3$ | H | $C_6H_5$ | H | 20 | (a) |

(a)Highly viscous pale yellow oil which shows no tendency to crystallize.

EXAMPLE 14 a. A mixture of 10.1 grams of benzaldehyde, 2-(3,4-dichlorophenyl)-1,1-dimethylsemicarbazone (prepared in Example 12 above), 25 milliliters water, and 15 milliliters of concentrated hydrochloric acid was heated with stirring while steam was passed through the mixture in order to remove the by-product benzaldehyde azeotropically. After 3 hours, the reaction mixture was cooled to 20° C and extracted with ether. The aqueous phase was concentrated to 75 milliliters and cooled to 5° C. Filtration gave 6.95 grams of colorless crystalline solid melting at 188°–190° C, representing an 81% yield of 2-(3,4-dichlorophenyl)-4,4-dimethylsemicarbazide hydrochloride.

b. To a stirred solution of 5.69 grams of the product of (a) above in 500 milliliters of 50% aqueous methanol was added 2.5 grams of thiophenecarboxaldehyde. This mixture was stirred for 5 hours at ambient temperature and concentrated to dryness. The residual oil was purified by silica chromatography to give 3.7 grams (54% yield) of 2-thiophenecarboxaldehyde, 2-(3,4-dichlorophenyl)-4,4-dimethylsemicarbazone, as a highly viscous yellow oil.

EXAMPLE 15

To a solution of 2.86 grams of 2-(3,4-dichlorophenyl)-4,4-dimethylsemicarbazide hydrochloride, prepared in 14 a) above, in 100 milliliters of water was added 3.0 grams of chloral hydrate. This mixture was stirred at ambient temperature for 5 hours. The yellow oil which had separated eas extracted into ether and dried. Evaporation of the ether gave 2.5 grams of chloral, 2-(3,4-dichlorophenyl)-4,4-dimethylsemicarbazone in 66% yield as a yellow viscous oil.

EXAMPLE 16 a. A mixture of 34.0 grams of benzaldehyde, 4,4-dimethyl-2-(3-(trifluoromethoxy)phenylsemicarbazone (prepared in Example 11 above) in 400 milliliters of 6% aqueous hydrochloric acid and 100 milliliters of ethylene glycol was heated to the boiling point while steam was passed into the stirred reaction mixture for 6.5 hours to remove the benzaldehyde azeotropically. The reaction mixture was cooled to 10° C and made alkaline by the addition of 30% aqueous sodium hydroxide solution. Extraction with ether gave 27.0 grams of light brown viscous liquid, representing an 82% yield of 4,4-dimethyl-2-(3-trifluoromethoxyphenyl)semicarbazide.

b. To a stirred solution of 3 grams of the product of (a) above in 25 milliliters water was added a solution of 2.5 grams 5-nitrofurfuraldehyde in 25 milliliters methanol. This mixture was stirred at ambient temperature for 4 hours. The reaction mixture was poured over ice water and filtered to give 2.5 grams of 5-nitrofurfuraldehyde, 4,4-dimethyl-2-(3-trifluoromethoxy)phenyl)-semicarbazone, melting at 104°–106° C, in 66% yield.

EXAMPLE 17

Using the experimental procedure of Example 15, 5-nitrofurfuraldehyde, 4,4-dimethyl-2-phenylsemicarbazone, melting at 157°–159° C, was prepared in 25% yield.

EXAMPLE 18

Using the experimental procedure of Example 14, 2-furanyl carboxaldehyde, 2-(3-chloro, 4-fluorophenyl)-

4,4-dimethylsemicarbazone, was prepared in 92.2% yield.

EXAMPLE 19

Using the experimental procedure of Example 14, 2-thiophene carboxaldehyde, 2-(3-chloro-4-fluorophenyl)-4,4-dimethylsemicarbazone, melting point 81°-83°, was prepared in 65.9% yield.

EXAMPLE 20

To a solution of 16.3 grams of N-(benzylideneamino)-2',4'-dichlorocarbanilic acid chloride in 500 milliliters of benzene was added 68 grams of anhydrous dimethylamine. This addition was exothermic to 80° and was left stirring at ambient temperature for 18 hours. The product was filtered and the filtrate concentrated to 169 grams of amber syrup. 10 grams of the syrup were purified by silica chromatography and 7 grams of amber syrup collected which showed no tendency to crystallize.

EXAMPLE 21

Using the experimental procedure of Example 20, benzaldehyde, 2-(3-chloro-4-fluorophenyl)-4,4-dimethyl semicarbazone, was prepared in 95% yield as an amber syrup.

EXAMPLE 22

Using the experimental procedure of Example 20, benzaldehyde, 2-(4-chloro-3-(trifluoromethyl)phenyl)-4,4-dimethyl semicarbazone, 55% yield, was prepared as an amber syrup.

EXAMPLE 23

Using the experimental procedure of Example 20, 2-(4-fluoro-3-(trifluoromethyl)phenyl)-4,4-dimethyl semicarbazone was prepared (100% yield) as an amber syrup.

EXAMPLE 24

Using the experimental procedure of Example 20, benzaldehyde, 2-(2,4-dichlorophenyl)-4,4-dimethyl semicarbazone (96.7% yield) as an amber syrup.

EXAMPLE 25

Using the experimental procedure of Example 20, 2-furanyl carboxaldehyde, 2-phenyl-4,4-dimethyl semicarbazone was prepared (28% yield).

EXAMPLE 26

To a solution of 10 grams of 4,4-dimethyl-2-(3-chloro-4-fluorophenyl)semicarbazide in 200 milliliters of benzene was added 8.1 grams of m-trifluoromethylacetophenone. This mixture was stirred and heated at reflux for 18 hours. The solvent was removed and the residue purified by silica chromatography to give 13 grams (75.1 yield) of 2-trifluoromethylacetophenone, 4,4-dimethyl-2-(3-chloro-4-fluorophenyl) semicarbazone as an amber syrup.

EXAMPLE 27

Using the experimental procedure of Example 26, cyclohexanone, 4,4-dimethyl-2-(3-chloro-4-fluorophenyl)semicarbazone, (94% yield) was obtained as an amber syrup.

EXAMPLE 28

Using the experimental procedure of Example 26, cyclopentanone, 4,4-dimethyl-2-(3-chloro-4-fluorophenyl)semicarbazone (25.2% yield) was obtained as an amber syrup.

EXAMPLE 29

Using the experimental procedure of Example 26, 2-propanone, 4,4-dimethyl-2-(3-chloro-4-fluorophenyl)-semicarbazone (98.4%) was obtained as an amber syrup.

EXAMPLE 30

To a solution of 17.9 grams of 4,4-dimethyl-2-phenyl semicarbazide in 200 milliliters acetone was added 10 grams of magnesium sulfate. The mixture was stirred and heated to reflux for 8 hours. The mixture was then left at ambient temperature for 18 hours. The products were filtered and the filtrate concentrated to 21.9 grams of amber syrup (100% yield) having a refractory index of 0.25.

EXAMPLE 31

To a solution of 7.0 grams of 4,4-dimethyl-2-phenyl semicarbazide in 100 milliliters of benzene was added 4.5 grams of 4-pyridine carboxaldehyde followed by a catalytic amount of p-toluenesulfonic acid. The mixture was stirred and heated to reflux for 18 hours. The solvent was removed in vacuo. The residue was taken in ether and treated with charcoal and filtered through celite. The filtrate was concentrated in vacuo to 10.4 grams (99.0% yield) of amber syrup, N,N-dimethyl-1-phenyl-2-(4-pyridylmethylene) hydrazinecarboxamide, having a refractory index of 0.16.

EXAMPLE 32

Following the procedure of Example 31, N,N-dimethyl-1-phenyl-2-(2-pyridylmethylene) hydrazinecarboxamide was prepared (99.3% yield) as an amber syrup having a refractory index of 0.27.

EXAMPLE 33

To a solution of 11.6 grams 4,4-dimethyl-2-(3-chloro-4-fluorophenyl) semicarbazide in 200 milliliters benzene was added 11.6 grams of trifluoroacetaldehyde followed by a catalytic amount of p-toluenesulfonic acid. The mixture was stirred and heated to reflux for 18 hours. The solvent was removed in vacuo. The residue was purified by silica chromatography to give 2.0 grams (12.7% yield) of trifluoroacetaldehyde, 2-(3-chloro-4-fluorophenyl)-4,4-dimethylsemicarbazone as an amber syrup.

EXAMPLE 34

The pre-emergence herbicidal activity of the compounds of the invention was evaluated by planting seeds of watergrass and cress in soil treated with the test compounds at the rates of 25 and 2.5 pounds per acre. The planted soil was held under controlled conditions of temperature, moisture, and light for 13 to 14 days. The amount of germination was then noted and the effectiveness of the test compound was rated on the basis of an 0 to 9 scale, 0 rating indicating no effect, 9 indicating death of the seedlings or no germination.

The post-emergence activity of the compounds of this invention was evaluated by spraying 10-day old pigweed plants and 7-day old crabgrass plants with a liquid formulation of the test compound at the rates of 10 pounds and 1 pound per acre. The sprayed plants were held under controlled conditions for 10 to 11 days and the effect of the test chemical then evaluated visually, the results being rated on the 0 to 9 scale described above.

and shoots was noted, and the effectiveness of the test compound rated on the 0 to 9 scale described above wherein 9 indicates death of the plant.

The results of the tests are summarized in Table II and Table III.

TABLE II

| | Herbicidal Activity | | | | | | | | | | | | | | | |
|---|---|---|---|---|---|---|---|---|---|---|---|---|---|---|---|---|
| | Pre-emergence | | | | Post-emergence | | | | General | | | | | | | |
| | Watergrass | | Cress | | Crabgrass | | Pigweed | | Ryegrass | | | | Sowthistle | | | |
| Compound | 25 | 2.5 | 25 | 2.5 | 10 | 1 | 10 | 1 | Roots | | Shoots | | Roots | | Shoots | |
| of | lbs/ | lbs/ | lbs/ | lbs/ | lbs/ | lb/ | lbs/ | lb/ | | | | | | | | |
| Example | acre | acre | acre | acre | acre | acre | acre | acre | 10* | 1* | 10* | 1* | 10* | 1* | 10* | 1* |
| 1 | 0 | 0 | 8 | 0 | 7 | 0 | 5 | 0 | 0 | 0 | 1 | 0 | 7 | 0 | 7 | 0 |
| 7 | 9 | 0 | 9 | 8 | 8 | 0 | 5 | 0 | 7 | 0 | 6 | 3 | 7 | 2 | 8 | 5 |
| 7 | 9 | 3 | 9 | 7 | 6 | 4 | 7 | 4 | 7 | 0 | 7 | 5 | 9 | 6 | 9 | 7 |
| 17 | 7 | 2 | 9 | 7 | 9 | 0 | 7 | 0 | 7 | 3 | 7 | 0 | 8 | 7 | 8 | 7 |
| 13 | 7 | 0 | 9 | 8 | 9 | 3 | 6 | 0 | 5 | 0 | 7 | 3 | 6 | 3 | 8 | 0 |
| 21 | 7 | 4 | 9 | 9 | 9 | 4 | 9 | 7 | — | — | — | — | — | — | — | — |
| 20 | 0 | 0 | 6 | 0 | 0 | 0 | 5 | 3 | — | — | — | — | — | — | — | — |
| 33 | 4 | 0 | 8 | 1 | 0 | 0 | 8 | 0 | — | — | — | — | — | — | — | — |
| 8 | 9 | 0 | 9 | 3 | 3 | 0 | 6 | 0 | 8 | 6 | 8 | 2 | 7 | 5 | 8 | 6 |
| 10 | 9 | 0 | 9 | 5 | 8 | 0 | 9 | 5 | 8 | 0 | 8 | 2 | 9 | 0 | 9 | 0 |
| 11 | 8 | 1 | 9 | 5 | 9 | 0 | 7 | 1 | 7 | 0 | 6 | 0 | 8 | 6 | 8 | 5 |
| 16 | 7 | 3 | 9 | 0 | 9 | 5 | 6 | 0 | 8 | 6 | 8 | 4 | 8 | 6 | 8 | 7 |
| 3 | 0 | 0 | 7 | 5 | 2 | 1 | 0 | 0 | 7 | 5 | 6 | 0 | 5 | 0 | 0 | 0 |
| 4 | 3 | 0 | 6 | 2 | 9 | 6 | 9 | 4 | 7 | 3 | 7 | 0 | 9 | 3 | 8 | 0 |
| 12 | 5 | 1 | 9 | 9 | 9 | 0 | 9 | 0 | 8 | 6 | 8 | 7 | 8 | 3 | 9 | 2 |
| 12 | 9 | 0 | 9 | 7 | 9 | 0 | 9 | 0 | 9 | 7 | 9 | 8 | 9 | 9 | 9 | 9 |
| 14 | 8 | 0 | 9 | 0 | 9 | 0 | 9 | 9 | 7 | 6 | 8 | 7 | 7 | 6 | 9 | 8 |
| 15 | 8 | 0 | 9 | 7 | 9 | 2 | 9 | 9 | 6 | 5 | 7 | 6 | 9 | 5 | 9 | 7 |
| 15 | 9 | 0 | 9 | 7 | 8 | 0 | 9 | 0 | 9 | 5 | 9 | 6 | 9 | 5 | 9 | 7 |
| 9 | 2 | 0 | 9 | 7 | 8 | 0 | 8 | 1 | 7 | 0 | 7 | 0 | 8 | 0 | 8 | 0 |
| 9 | 0 | 0 | 9 | 6 | 8 | 3 | 4 | 4 | 4 | 2 | 7 | 4 | 9 | 0 | 9 | 3 |

*parts/million
— indicates no test

TABLE III

| | Herbicidal Activity | | | | | | | | | | | | | | | | | | |
|---|---|---|---|---|---|---|---|---|---|---|---|---|---|---|---|---|---|---|---|
| | Pre-emergence | | | | | | | | | | | | | | | | | | |
| | Watergrass | | Cress | | Soybean | | G.Sorgh. | | Cotton | | | | | | | | | | |
| Compound | 2.5 | 25 | 2.5 | 25 | 2.5 | 25 | 2.5 | 25 | 25 | Post-emergence | | | | | | | | | |
| of | lbs/ | lbs/ | lbs/ | lbs/ | lbs/ | lbs/ | lbs/ | lbs/ | lbs/ | Crabgrass | | Pigweed | | Soybean | | G.Sorgh | | Cotton | |
| Example | acre | acre | acre | acre | acre | acre | acre | acre | acre | 1* | 10* | 1* | 10* | 1* | 10* | 1* | 10* | 10* | |
| 26 | 5 | 7 | 9 | 9 | — | — | — | — | — | 0 | 9 | 0 | 9 | — | — | — | — | — | |
| 19 | 3 | 5 | 7 | 8 | — | — | — | — | — | 2 | 9 | 0 | 9 | — | — | — | — | — | |
| 28 | 2 | 7 | 7 | 9 | 8 | — | — | — | — | 8 | 8 | 2 | 9 | — | — | — | — | — | |
| 22 | 0 | 5 | 7 | 9 | — | 7 | — | 7 | 1 | 1 | 8 | 1 | 9 | — | 3 | — | 3 | 0 | |
| 5 | 0 | 5 | 2 | 9 | — | 8 | — | 8 | 0 | 0 | 1 | 1 | 8 | — | 2 | — | 3 | 0 | |
| 6 | 0 | 6 | 8 | 9 | — | 5 | — | 3 | 0 | 1 | 7 | 2 | 7 | — | 5 | — | 0 | 2 | |
| 23 | 0 | 7 | 4 | 8 | — | 1 | — | 1 | 0 | 0 | 8 | 7 | 8 | — | 8 | — | 8 | 6 | |
| 29 | 6 | 6 | 9 | 9 | — | 8 | — | 8 | 8 | 3 | 3 | 0 | 2 | — | 5 | — | 3 | 0 | |
| 18 | 5 | 6 | 9 | 9 | — | 7 | — | 8 | 1 | 1 | 7 | 7 | 9 | — | 5 | — | 6 | 6 | |
| 27 | 6 | 6 | 9 | 9 | — | 7 | — | 8 | 9 | 5 | 5 | 2 | 6 | — | 3 | — | 2 | 0 | |
| 24 | 0 | 0 | 0 | 0 | — | — | — | — | — | 1 | 3 | 0 | 2 | — | — | — | — | — | |
| 30 | 3 | 7 | 7 | 8 | — | 8 | — | 7 | 6 | 0 | 1 | 1 | 7 | — | 5 | — | 0 | 3 | |
| 31 | 0 | 2 | 1 | 9 | — | 6 | — | 5 | 1 | 0 | 1 | 0 | 1 | — | 4 | — | 0 | 4 | |
| 32 | 0 | 3 | 1 | 6 | — | 2 | — | 1 | 0 | 0 | 1 | 0 | 1 | — | — | — | — | — | |

*parts/million
—indicates no test above.

The general phytotoxicity of the compounds was evaluated by planting ryegrass and sowthistle plants in culture solutions treated with the test compounds at the rate of 10 parts per million and 1 part per million solution. The plants were held under controlled conditions for 10 to 11 days. The amount of growth of the roots

EXAMPLE 35

The pre-emergence herbicidal effect of the compounds of the invention was further tested on eight weeds. The results of the pre-emergence tests are given in Table IV.

TABLE IV

| | Pre-emergence Herbicide Plant - $LD_{95}$ (lb/acre) | | | | | | | | |
|---|---|---|---|---|---|---|---|---|---|
| Compound of Example | Ryegrass | Cheatgrass | Crabgrass | Watergrass | Pigweed | Mustard | Sowthistle | Curly Dock | Soybean |
| 7 | 2.1 | 2.5 | 6.0 | 3.5 | 1.0 | <1.0[1] | <1.0 | 1.5 | — |
| 8 | 1.3 | 4.5 | 1.8 | 2.5 | 1.0 | <1.0 | <1.0 | 1.0 | — |
| 12 | <1.0 | >10[2] | 1.3 | 1.5 | 1.2 | 2.0 | <1.0 | <1.0 | — |
| 9 | >10 | 9.0 | >10 | >10 | 8.0 | 8.0 | 9.0 | >10 | — |
| 21[3] | — | >5 | >5 | >5 | >5 | 3.3 | — | 4.4 | — |
| 21[4] | — | — | — | — | 0.9 | <0.5 | — | <0.5 | — |
| 26[3] | — | — | 3.8 | >5 | >5 | 3.8 | — | >5 | >5 |
| 26[4] | — | — | 0.7 | 1.6 | <0.5 | 0.9 | — | <0.5 | 0.5 |
| 19[3] | — | — | >5 | >5 | >5 | 3.3 | — | >5 | >5 |

TABLE IV-continued

| Compound of Example | Pre-emergence Herbicide Plant - LD$_{95}$ (lb/acre) | | | | | | | |
|---|---|---|---|---|---|---|---|---|
| | Ryegrass | Cheatgrass | Crabgrass | Watergrass | Pigweed | Mustard | Sowthistle | Curly Dock | Soybean |
| 19[4] | — | — | 0.7 | 2.1 | <0.5 | 2.1 | — | 0.7 | >2.8 |
| 28[3] | — | — | <2.8 | >5 | >5 | <2.8 | — | <2.8 | >5 |
| 28[4] | — | — | 0.5 | 1.2 | <0.5 | 0.8 | — | <0.5 | 1.2 |

[1] The symbol < means "less than"
[2] The symbol > means "greater than"
[3] Testing done on Webster soil
[4] Testing done on Hanford soil
— indicates no test

I claim as my invention:

1. A compound of the formula

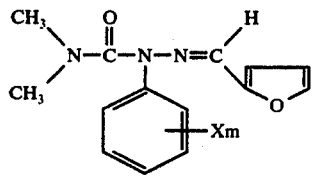

wherein X is chlorine, and m is 2.

2. A compound of the formula

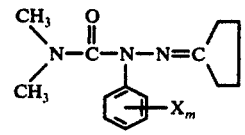

wherein X is trifluoromethyl and m is 1.

3. A compound of the formula

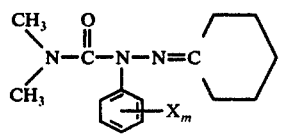

wherein m is 2 and one of X is chlorine and the other is fluorine.

4. A compound of the formula wherein m is 2 and one of X is chlorine and the other is fluorine.

5. A compound of the formula wherein m is 2 and 1 of X is chlorine and the other is fluorine.

* * * * *